United States Patent [19]

Chen et al.

[11] 4,112,056

[45] Sep. 5, 1978

[54] PREPARATION OF ZEOLITES

[75] Inventors: Nai Yuen Chen, Titusville; Joseph Nicolas Miale, Lawrenceville, both of N.J.; William Joseph Reagan, Yardley, Pa.

[73] Assignee: Mobil Oil Corporation, New York, N.Y.

[21] Appl. No.: 792,741

[22] Filed: May 2, 1977

[51] Int. Cl.$^2$ .................... C01B 33/28; C07F 5/06
[52] U.S. Cl. .................. 423/329; 252/431 N; 252/455 Z; 260/326.61; 260/448 C
[58] Field of Search ............... 423/329, 330, 328, 118; 252/455 Z, 431 N; 260/448 C, 326.61; 208/111, 120

[56] References Cited

U.S. PATENT DOCUMENTS

| | | | |
|---|---|---|---|
| 3,071,434 | 1/1963 | Frilette et al. | 423/329 |
| 3,433,589 | 3/1969 | Ciric et al. | 423/329 |
| 3,702,886 | 11/1972 | Argauer et al. | 423/328 |
| 3,709,979 | 1/1973 | Chu | 423/328 |
| 3,832,449 | 8/1974 | Bosinski et al. | 423/328 |
| 3,947,482 | 3/1976 | Albers et al. | 260/448 C |
| 4,025,572 | 5/1977 | Lago | 423/328 X |

*Primary Examiner*—Edward J. Meros
*Attorney, Agent, or Firm*—Charles A. Huggett; Dennis P. Santini

[57] ABSTRACT

An improved method is provided for preparing a crystalline aluminosilicate zeolite having a high silica/alumina mole ratio which comprises adding a source of aluminum ions to a silica-rich amorphous reaction medium at a rate whereby the concentration of aluminum ions in the amorphous phase of the preparation is maintained at steady state during crystallization. Crystallization time is substantially shortened by the present improved method and zeolites synthesized by way of the present improved method exhibit improved steam stability.

Also provided are improved crystalline aluminosilicate zeolites prepared by way of the present improved method of synthesis and organic compound conversion therewith.

15 Claims, No Drawings

PREPARATION OF ZEOLITES

BACKGROUND OF THE INVENTION

1. Field of the Invention

This invention relates to an improved method for preparation of certain zeolites having a high silica/alumina mole ratio, i.e. greater than about 10. The improvement resides in adding a source of aluminum ions to a silica-rich amorphous reaction medium at a slow and controlled rate whereby the concentration of aluminum ions in the amorphous phase of the reaction mixture is maintained at steady state during crystallization.

More particularly, this invention relates to the above improved method of preparation of certain zeolites whereby crystallization time is substantially reduced from that required when conventional prior art methods of preparation are utilized and the resulting zeolite exhibits somewhat improved steam stability, i.e. stability toward steam deactivation and dealuminization.

Even more particularly, this invention relates to organic compound conversion, such as, for example, catalytic conversion of oxygenates, such as methanol, and syn-gas conversion where water is always present during reaction, with the improved zeolite product of the present improved method as a catalyst.

2. Discussion of Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as (Ca/2), (Sr/2), Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. 3,247,195), zeolite ZK-4 (U.S. Pat. No. 3,314,752) and zeolite ZSM-5 (U.S. Pat. No. 3,702,886) merely to name a few.

Applicants know of no prior art methods of zeolite preparation utilizing the present improvement. In fact, the present improved method of zeolite preparation is distinctly different from the current practice in the synthesis of zeolites having a silica/alumina mole ratio greater than 10.

SUMMARY OF THE INVENTION

An improved method for preparing an improved crystalline aluminosilicate zeolite having a high silica/alumina mole ratio and exhibiting improved steam stability is provided which comprises forming a silica-rich reaction mixture containing sources of an alkali metal oxide, any organic nitrogen-containing oxides required for preparation of the particular zeolite to be synthesized, an oxide of silicon and water, and adding thereto one or more sources of aluminum ions at a slow and controlled rate whereby the concentration of aluminum ions in the amorphous phase of the reaction mixture is maintained at steady state during crystallization. Reaction conditions include heating the reaction mixture in the amorphous phase at steady state to a temperature of from about 180° F to about 400° F for a period of time of from about 2 hours to about 30 days. At any given reaction temperature, crystallization time is significantly reduced by the present improved method when compared to conventional techniques for preparing the same zeolite.

DESCRIPTION OF SPECIFIC EMBODIMENTS

The present invention offers a means of synthesizing certain crystalline aluminosilicate zeolites having high silica/alumina mole ratios and improved aging characteristics. Improved zeolites which may be prepared in accordance herewith include those which will crystallize from silica-rich reaction mixtures, such as, for example, ZSM-5, ZSM-11, ZSM-12 and ZSM-23.

Zeolite ZSM-5 and the conventional preparation thereof are described in U.S. Pat. No. 3,702,886, the disclosure of which is incorporated by reference. Zeolite ZSM-11 and the conventional preparation thereof are described in U.S. Pat. No. 3,709,979, the disclosure of which is incorporated herein by reference. Zeolite ZSM-12 and the conventionl preparation thereof are described in U.S. Pat. No. 3,832,449, the disclosure of which is incorporated herein by reference.

Zeolite ZSM-23 and the conventional preparation thereof are more particularly described in U.S. Application Ser. No. 739,414, filed Nov. 8, 1976. This zeolite can be identified, in terms of mole ratios of oxides and in the anhydrous state, as follows:

$$(0.58-3.4)M_{(2/n)}O : Al_2O_3 : (40-250)SiO_2$$

where M is at least one cation and n is the valence thereof. It will be noticed that the ratio of $M_{(2/n)}O$ may exceed unity in this material. This is probably due to the occlusion of excess organic species, used in the preparation of ZSM-23, within the zeolite pores.

In a preferred synthesized form, zeolite ZSM-23 has a formula, in terms of mole ratios of oxides and in the anhydrous state, as follows:

$$(0.5-3.0)R_2O : (0.08-0.4)M_2O : Al_2O_3 : (40-250)SiO_2$$

wherein R is an organic nitrogen-containing cation derived from pyrrolidine and M is an alkali metal cation. It will be noticed that in this preferred form the ratio of $R_2O$ to $Al_2O_3$ may exceed unity, probably due to the occlusion of excess nitrogen-containing organic species ($R_2O$) within the zeolite pores.

The synthetic ZSM-23 zeolite possesses a definite distinguishing crystalline structure whose X-ray diffraction pattern shows substantially the significant lines set forth in Table I.

TABLE I

| d(A) | I/Io |
|---|---|
| 11.2 ± 0.23 | Medium |
| 10.1 ± 0.20 | Weak |
| 7.87 ± 0.15 | Weak |
| 5.59 ± 0.10 | Weak |
| 5.44 ± 0.10 | Weak |
| 4.90 ± 0.10 | Weak |
| 4.53 ± 0.10 | Strong |
| 3.90 ± 0.08 | Very Strong |
| 3.72 ± 0.08 | Very Strong |
| 3.62 ± 0.07 | Very Strong |
| 3.54 ± 0.07 | Medium |
| 3.44 ± 0.07 | Strong |
| 3.36 ± 0.07 | Weak |
| 3.16 ± 0.07 | Weak |
| 3.05 ± 0.06 | Weak |
| 2.99 ± 0.06 | Weak |
| 2.85 ± 0.06 | Weak |
| 2.54 ± 0.05 | Medium |
| 2.47 ± 0.05 | Weak |
| 2.40 ± 0.05 | Weak |
| 2.34 ± 0.05 | Weak |

These values were determined by standard techniques. The radiation was the K-alpha doublet of copper, and a Geiger counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d(A), the interplanar spacing in Angstrom units, corresponding to the recorded lines, were calculated.

Zeolite ZSM-23 can be conventionally synthesized by preparing a solution containing sources of an alkali metal oxide, preferably sodium oxide, sources of nitrogen-containing cation, preferably pyrrolidine, an oxide of aluminum, an oxide of silicon and water and having a composition, in terms of mole ratios of oxides, falling within the following ranges:

| | |
|---|---|
| $\frac{R^+}{R^+ + M^+}$ | 0.85 – 0.95 |
| $OH^-/SiO_2$ | 0.01 – 0.049 |
| $H_2O/OH^-$ | 200 – 600 |
| $SiO_2/Al_2O_3$ | 55 – 70 | wherein R is an organic nitrogen-containing cation and M is an alkali metal ion, and maintaining the mixture until crystals of the zeolite are formed. The quantity of $OH^-$ is calculated only from the inorganic sources of alkali without any organic base contribution. Thereafter, the crystals are separated from the liquid and recovered. Typical reaction conditions consist of heating the foregoing reaction mixture to a temperature above 280° F to about 400° F for a period of time of from about 6 hours to about 14 days. A more preferred temperature range is from about 300° F to about 375° F with the amount of time at a temperature in such range being from about 24 hours to about 11 days.

The digestion of the gel particles is carried out until crystals form. The solid product is separated from the reaction medium, as by cooling the whole to room temperature, filtering and water washing.

The crystalline product is dried, e.g. at 230° F, for from about 8 to 24 hours. Of course, milder conditions may be employed if desired, e.g. room temperature under vacuum.

The conventional synthesis of zeolite is generally carried out in a batch process. The starting gel material usually has a composition different from that of the crystalline product. Thus, the composition of the amorphous phase changes continuously during the crystallization process. For example, the chemical composition of a ZSM-5 synthesis gel has a 94 $SiO_2/Al_2O_3$ mole ratio, while the product therefrom is a 70 $SiO_2/Al_2O_3$ mole ratio ZSM-5. The $Al_2O_3$ concentration in the amorphous phase is higher at the beginning than at the end of the crystallization. The effect of the changing aluminum ion concentration in the amorphous phase on the distribution of tetracoordinate aluminum in the crystalline product has apparently not received attention prior to the present invention.

Although not wishing to be bound by a theoretical analysis, it was thought that the stability of a zeolite might be improved by a procedure to produce more isolated aluminum lattice sites, i.e. maintaining a constant aluminum ion concentration in the amorphous phase during crystallization. The present invention resulted from an investigation of such theory.

In the present improved method of zeolite preparation, an amorphous mixture, rich in silica, is prepared respecting the particular zeolite product to result therefrom. This mixture will, in general, be composed of sources of an alkali metal oxide, any organic nitrogen-containing oxides required for the particular zeolite to be synthesized, an oxide of silicon and water. In general, this silica-rich reaction mixture may have a composition, in terms of mole ratios of oxides, as follows:

| | | |
|---|---|---|
| $OH^-/SiO_2$ | = | 0.01 – 0.5 |
| $Al_2O_3/SiO_2$ | = | 0 – 0.01 |
| $H_2O/OH^-$ | = | 50 – 500 |
| $M_2O/SiO_2$ | = | 0.01 – 1.0 |
| $R_2O/SiO_2$ | = | 0.01 – 0.5 | wherein M is an alkali metal ion, such as sodium, and R is an organic nitrogen-containing cation.

Specifically, as a non-limiting example, when ZSM-5 is the desired product, the silica-rich mixture may be composed of sources of an alkali metal oxide, organic nitrogen-containing oxide, an oxide of silicon and water and may have a composition, in terms of mole ratios of oxides, as follows:

| | | |
|---|---|---|
| $OH^-/SiO_2$ | = | 0.1 |
| $Al_2O_3/SiO_2$ | = | 0 |
| $H_2O/OH^-$ | = | 300 |
| $M_2O/SiO_2$ | = | 0.9 |
| $R_2O/SiO_2$ | = | 0.05 | wherein M is an alkali metal ion and R is a tetrapropylammonium ion.

When, as a non-limiting example, ZSM-11 is the desired product, the silica-rich mixture may be composed of sources of an alkali metal oxide, organic nitrogen-containing oxide, an oxide of silicon and water having a composition, in terms of mole ratios of oxides, as follows:

| | | |
|---|---|---|
| $OH^-/SiO_2$ | = | 0.2 |
| $Al_2O_3/SiO_2$ | = | 0–0.001 |
| $H_2O/OH^-$ | = | 134 |
| $M_2O/SiO_2$ | = | 0.2 |
| $R_2O/SiO_2$ | = | 0.19 | wherein M is an alkali metal ion and R is a tetrabutylammonium or tetrabutylphosphonium ion.

When, as a non-limiting example, ZSM-12 is the desired product, the silica-rich mixture may be composed of sources of an alkali metal oxide, organic nitrogen-containing oxide, an oxide of silicon and water having a composition, in terms of mole ratios of oxides, as follows:

| | | |
|---|---|---|
| $OH^-/SiO_2$ | = | 0.2 |
| $Al_2O_3/SiO_2$ | = | 0–0.001 |
| $H_2O/OH^-$ | = | 78 |
| $M_2O/SiO_2$ | = | 0.11 |
| $R_2O/SiO_2$ | = | 0.1 | wherein M is an alkali metal ion and R is a tetraethylammonium ion.

When, as a non-limiting example, ZSM-23 is the desired product, the silica-rich mixture may be composed of sources of an alkali metal oxide, organic nitrogen-containing oxide, an oxide of silicon and water having a composition, in terms of mole ratios of oxides, as follows:

| | | |
|---|---|---|
| $OH^-/SiO_2$ | = | .049 |
| $Al_2O_3/SiO_2$ | = | 0–.001 |
| $H_2O/OH^-$ | = | 208 |
| $M_2O/SiO_2$ | = | .02 |
| $R_2O/SiO_2$ | = | .14 | wherein M is an alkali metal ion and R is a cation derived from pyrrolidine.

To the silica-rich mixture is then added a source of aluminum ions in a manner whereby the concentration of aluminum ions in the amorphous phase of the reaction mixture is maintained at a steady state during crystallization from the reaction mixture. By steady state it is meant that the concentration of aluminum in the amorphous phase of the reaction mixture (i.e., total aluminum concentration less aluminum in the zeolite crystal) is maintained at a constant value by replenishing it at the same rate as the rate of zeolite crystallization.

The source of aluminum ions may be any of a number of recognized compounds of aluminum, such as, for example, sulfates, oxides, aluminates and others. Specific examples of such sources include sodium aluminate and aluminum sulfate.

When the present improved method of preparing certain high silica/alumina zeolites is followed, an increase in the rate of crystallization at a given reaction temperature is achieved when compared to conventional prior art methods of manufacture for a given zeolite. Such rates of crystallization may be improved by as much as ten times or more depending upon such factors as the organic cations, temperature, pressure, aluminum concentration in the starting mixture and $SiO_2/H_2O$ ratio. This faster rate of crystallization allows for numerous benefits, some of which include:

1. The crystallization of lower $SiO_2/Al_2O_3$ mole ratio zeolites, e.g. ZSM-5, which take a longer time to synthesize by conventional methods, may be accelerated by the present improved procedure.
2. The high temperature autoclave synthesis used in the commercial production of some zeolites, e.g. ZSM-5, may not be necessary if the present improved procedure is adopted.

The improved zeolites prepared by the present improved method may be used for organic compound conversion in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table, especially rare earth metals. However, in the case of Group IA metals, the cation content should in no case be so large as to effectively inactivate the catalyst.

As in the case of many catalysts, it is desirable to incorporate the improved catalyst prepared by the present improved method with another material resistant to the temperature and other conditions employed in some organic compound conversion processes. Such matrix materials include active and inactive materials and synthetic or naturally occurring zeolites as well as inorganic material such as clays, silica and/or metal oxides. The latter may be either naturally occurring or in the form of gelatinous precipitates, sols or gels including mixtures of silica and metal oxides. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e. clays, oxides, etc., function, in part, as binders for the catalyst. It may be desirable to provide a catalyst having good crush strength so it may be used in a process where the catalyst is subjected to rough handling, such as in a fluidized system, which may tend to break the catalyst down into powder-like materials which cause problems in processing.

Naturally occurring clays which can be composited with the improved zeolites prepared hereby include the montmorillonite and kaolin families, which include the sub-bentonites and the kaolins commonly known as Dixie, McNammee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites made hereby can be composited with one or more porous matrix materials such as alumina, silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel. A mixture of these components, one with the other and/or with a clay, could also be used. The relative proportions of zeolite and inorganic oxide gel matrix and/or clay vary widely with the crystalline aluminosilicate content ranging from about 1 to about 90 percent by weight and more usually in the range of about 2 to about 50 percent by weight of the composite.

Zeolites prepared by the present improved method are valuable catalysts in various organic compound, e.g.

hydrocarbon compounds and oxygenates such as methanol, conversion processes. Such processes include, for example, alkylation of aromatics with olefins, aromatization of normally gaseous olefins and paraffins, aromatization of normally liquid low molecular weight paraffins and olefins, isomerization of aromatics, paraffins and olefins, disproportionation of aromatics, transalkylation of aromatics, oligomerization of olefins and cracking and hydrocracking. All of the foregoing catalytic processes are of value since they result in upgrading of the organic charge being processed.

The process for upgrading reformates wherein a zeolite prepared in accordance herewith is employed as catalyst generally involves contact during processing with a reformate or reformer effluent, with or without added hydrogen, at a temperature between 500° F and about 1100° F and preferably between about 550° F and about 1000° F. The reaction pressure in such operation is generally within the range of about 25 and about 2000 psig and preferably about 50 to about 1000 psig. The liquid hourly space velocity, i.e. the liquid volume of hydrocarbon per hour per volume of catalyst, is between about 0.1 and about 250, and preferably between about 1 and 100. Although hydrogen is not essential to this process, when it is used the molar ratio of hydrogen to hydrocarbon charge employed is between about 0.1 and about 80 and preferably between about 1 and about 10.

Oligomerization of olefins, i.e. olefins having 2 to 10 carbon atoms, is effectively carried out with the zeolite prepared in accordance herewith as catalyst. Such reaction is suitably effected at a temperature between about 550° F and about 1150° F, a pressure between about 0.01 and about 1000 psig utilizing a weight hourly space velocity within the approximate range of 0.1 to 1000.

Alkylation of aromatic hydrocarbons, e.g. benzene, with an alkylating agent such as an alkyl halide, an alcohol or an olefin, is also readily effected in the presence of the presently made zeolite as catalyst with reduced aging. Alkylation conditions include a temperature between about 400° F and about 1000° F, a pressure between about 25 and about 1000 psig utilizing an aromatic hydrocarbon/alkylating agent mole ratio of 2 to 200 and an alkylating agent weight hourly space velocity within the approximate range of 0.5 to 50.

Xylene isomerization is another reaction suitably conducted in the presence of the zeolite made in accordance herewith as catalyst. Isomerization conditions include a temperature between about 300° F and about 900° F, a pressure between about 25 and about 1000 psig utilizing a weight hourly space velocity within the approximate range of 0.2 to 100.

Aromatics, such as, for example, toluene, may be disproportionated in the presence of the presently made zeolite under a temperature of from about 450° F to about 1100° F, a pressure of from about 50 psig to about 800 psig and a liquid hourly space velocity within the approximate range of about 0.1 to about 20. Aliphatic hydrocarbons may also be disproportionated in the presence of zeolite prepared by the present improved method at a temperature of from about 350° F to about 900° F, a pressure between 0 and 3,000 psig and a liquid hourly space velocity of between about 0.01 and about 5.

When the conversion of organic compounds with the presently made zeolite as catalyst is cracking, catalytic conversion conditions should be maintained within certain ranges, including a temperature of from about 700° F to about 1200° F, preferably from about 800° F to about 1000° F, a pressure of from about atmospheric to about 200 psig, and a liquid hourly space velocity of from about 0.5 $hr^{-1}$ to about 50 $hr^{-1}$, preferably from about 1 $hr^{-1}$ to about 10 $hr^{-1}$. When the conversion is hydrocracking, catalytic conversion conditions should be maintained within somewhat different ranges, including a temperature of from about 400° F to about 1000° F, preferably from about 500° F to about 850° F, a pressure of from about 500 psig to about 3500 psig, a liquid hourly space velocity of from about 0.1 $hr^{-1}$ to about 10 $hr^{-1}$, preferably from about 0.2 $hr^{-1}$ to about 5 $hr^{-1}$, and a hydrogen/hydrocarbon ratio of from about 1000 scf/bbl to about 20,000 scf/bbl, preferably from about 3,000 scf/bbl to about 10,000 scf/bbl.

When the conversion of organic compounds with the zeolite prepared in accordance with the present improved method as catalyst involves oxygenates, still different reaction conditions are required. For example, for conversion of methanol to hydrocarbons, the conversion temperature must be maintained at from about 500° F to about 900° F, the conversion pressure at from about 30 psig to about 500 psig and hydrogen or recycle gas may be added to the charge stock.

It may be desirable in some instances to add a hydrogenation/dehydrogenation component to the zeolite prepared in accordance herewith for use as catalyst. The amount of the hydrogenation/dehydrogenation component employed is not narrowly critical and can range from about 0.01 to about 30 weight percent based on the entire catalyst. A variety of hydrogenation components may be combined with either the zeolite and/or matrix in any feasible manner which affords intimate contact of the components, employing well known techniques such as base exchange, impregnation, coprecipitation, cogellation, mechanical admixture of one component with the other and the like. The hydrogenation component can include metals, oxides and sulfides of metals of the Periodic Table which fall in Group VI-B including chromium, molybdenum, tungsten and the like; Group II-B including zinc and cadmium; Group VIII including cobalt, nickel, platinum, palladium, ruthenium, rhodium, osmium and iridium; Group IV-A such as germanium and tin and combinations of metals, sulfides and oxides of metals of Group VI-B and VIII, such as nickel-tungsten-sulfide, cobalt oxide-molybdenum oxide and the like. Pre-treatment before use varies depending on the hydrogenation component present. For example, with components such as nickel-tungsten, cobalt-molybdenum, platinum and palladium, the catalyst may desirably be sulfided. With metals like platinum or palladium, a hydrogenation step may also be employed. These techniques are well known in the art and are accomplished in a conventional manner.

In order to more fully illustrate the nature of the invention and the manner of practicing same, the following examples are presented. In these examples, the sodium silicate contained 28.5 wt. % $SiO_2$, 7.7 wt. % $Na_2O$ and 63.7 wt. % $H_2O$ and the sodium aluminate source of alumina contained 43.5 wt. % $Al_2O_3$, 30.0 wt. % $Na_2O$ and 26.5 wt. % $H_2O$.

EXAMPLE 1

Five preliminary solutions were individually prepared to be as follows:

| Solution A | 2.5 | g | Sodium aluminate |

-continued

|            |       |   |                          |
|------------|-------|---|--------------------------|
|            | 0.17  | g | NaOH                     |
|            | 66    | g | $H_2O$                   |
| Solution B | 211.2 | g | sodium silicate          |
|            | 264   | g | $H_2O$                   |
| Solution C | 26.4  | g | Tetrapropylammonium bromide |
|            | 132   | g | $H_2O$                   |
| Solution D | 21    | g | $H_2SO_4$                |
|            | 66    | g | $H_2O$                   |
| Solution E | 79.2  | g | NaCl                     |
|            | 95    | g | $H_2O$                   |

In a conventional zeolite preparation, solution B was combined with solution C and the resultant solution combined with the entire solution A. Solution D was then added to the mixture slowly with vigorous agitation. The mixing was continued until the mixture was a homogeneous gel. Solution E was then added with stirring. The reaction mixture had the following mole ratios:

| | |
|---|---|
| $SiO_2/Al_2O_3$ | 94.1 |
| $H_2O/OH^-$ | 273 |
| $(M_2O+R_2O)/SiO_2$ | 0.995 |
| $M_2O/SiO_2$ | 0.96 |
| $R_2O/M_2O$ | 0.053 |
| $OH^-/SiO_2$ | 0.15 |

The reaction mixture was then transferred to a 3 liter pyrex flask and maintained at 100° C to crystallize. Periodically, samples were removed from the reaction mixture, washed free of excess alkali and dried. X-ray diffraction analysis of the product samples showed that it took at least 50 days to obtain 100 weight percent crystalline zeolite (in this case ZSM-5) with a $SiO_2/Al_2O_3$ mole ratio of 70.

EXAMPLES 2–7

The preliminary solutions of Example 1 were combined in different ways to make up a first solution rich in silica, i.e. silicate gel, and a second solution containing a source of aluminum ions, i.e. aluminate solution. These first and second solutions were comprised of the components indicated in Table II.

heights of the reflection at 2 theta = 23.1. The amount of second solution to be added was estimated from the percentage of ZSM-5 crystals found in the reaction mixture, and the projected rate of increase of crystallinity for a period of 12 hours. In each case, any excess concentration of aluminum species in the gel phase was kept at a minimum.

Results

1. Examples 2 and 3:

These two highly alkaline silicate gel first solutions ($OH^-/SiO_2 = 0.52$) separated upon heating to a solid mass of glass. Addition of the second solutions did not dissolve or redisperse the glass. Both preparations were abandoned after failure to obtain any zeolite crystallization after three weeks.

2. Examples 4 and 5:

In Example 4, thirty percent of the acidic aluminate solution (second solution) was added to the refluxing silicate gel first solution on the first day. The rate of crystallization was unexpectedly high. By the fourth day, X-ray analysis indicated an 83% crystallinity. Analysis of the solid product after thorough washing gave a $SiO_2/Al_2O_3$ ratio of 114. On the fourth day, 80 percent of the second, i.e. aluminate, solution was added; another ten percent was added on the sixth day; the addition was completed on the ninth day, and the crystallization was continued to the 21st day. The X-ray analysis indicated a ZSM-5 concentration of 89%. The elemental analysis of the final product was as follows:

| Component | Wt% |
|-----------|------|
| $SiO_2$   | 90.4 |
| $Al_2O_3$ | 2.19 |
| Na        | 1.64 |
| N         | 0.57 |
| C         | 5.23 |

In this example, there was no appreciable increase in crystallinity from the third day on and yet the $SiO_2/Al_2O_3$ ratio of the product changed significantly, i.e. at day 3, $SiO_2/Al_2O_3$ ratio was 114; at day 4, $SiO_2/Al_2O_3$ ratio was 74; at day 19, $SiO_2/Al_2O_3$ ratio was 70. Thus the

TABLE II

| Example No. | 2 | 3 | 4 | 5 | 6 | 7 |
|-------------|---|---|---|---|---|---|
| First Solution Composition From Preliminary Solutions A–E of Example 1 | B+C+E | B+C | B+C+ 77wt.%(D+E) | B+C+ D+E | B+D | B+D |
| Reaction Mixture Composition of Amorphous First Solution | | | | | | |
| $H_2O/OH^-$ | 64 | 55 | 165 | 255 | 430 | 430 |
| $(M_2O+R_2O)/SiO_2$ | 0.995 | 0.32 | 0.83 | 0.995 | 0.27 | 0.27 |
| $M_2O/SiO_2$ | 0.945 | 0.27 | 0.78 | 0.945 | 0.27 | 0.27 |
| $R_2O/SiO_2$ | 0.05 | 0.05 | 0.05 | 0.05 | 0 | 0 |
| $OH^-/SiO_2$ | 0.52 | 0.52 | 0.22 | 0.06 | 0.05 | 0.05 |
| Second Solution Composition From Preliminary Solutions A–E of Example 1 | A+D | A+D+E | A+23wt.% (D+E) | A | A+C+E | A+C+E |

The various first solution silicate gels were refluxed and stirred at atmospheric pressure in three liter Pyrx round bottom flasks. The various second solutions were added periodically at a rate whereby the concentration of aluminum ions in the amorphous phase was about steady state. Aliquotes of the reaction mixtures were taken daily, filtered, washed, and analyzed for percent crystallinity. The X-ray powder diffraction data were obtained with CuK alpha radiation on a Siemens X-ray diffractometer. The zeolite crystallinity (in these examples ZSM-5) was estimated from the relative peak crystals must have undergone structural rearrangement as new source of aluminum ions was added to the reaction mixture.

In Example 5, ten percent of the aluminate solution (second solution) was added each day for the first three days. On the third day, X-ray analysis indicated a 29 percent crystallinity. Fifty-seven percent of the aluminate solution was then added at that time. Complete crystallization of zeolite ZSM-5 was achieved on the tenth day. The X-ray analysis indicated a ZSM-5 concentration of 100 percent. The elemental analysis of the product is shown below:

| Component | Wt% |
|---|---|
| $SiO_2$ | 89.7 |
| $Al_2O_3$ | 2.03 |
| Na | 1.30 |
| N | 0.78 |
| C | 6.43 |

3. Examples 6 and 7:

In these examples, the first solution of the reaction mixture contained only the silicate and the sulfuric acid, while the tetrapropyl ammonium bromide, NaCl and sodium aluminate solutions were combined as second solution and added periodically to the refluxing first solution silicate gel mixture. In Example 6, after four days and 30 percent addition of the second solution, crystallization had not begun. However, over the next two days, the product exceeded 100 percent crystallinity. The experiment was terminated at this point. Analysis of the product gave a $SiO_2/Al_2O_3$ ratio of 175. In Example 7, the reaction mixture was refluxed with the addition of only ten percent of the second solution until nine percent crystallinity was observed on the fifth day. On the sixth day, the crystallinity rose to 31 percent, and 60 percent of the second solution was added. The excess aluminate in the amorphous phase of Example 7 at that point decidedly retarded the crystallization process. In fact, the crystallization lagged behind the addition rate for Example 7 and 100 percent crystallinity was achieved after 26 days. Elemental analysis of the final product from Example 7 was as follows:

| Component | Wt% |
|---|---|
| $SiO_2$ | 92.5 |
| $Al_2O_3$ | 2.25 |
| Na | 0.76 |
| N | 0.91 |
| C | 7.70 |

Except for the highly alkaline preparations, the synthesis of zeolite crystals was achieved by the controlled periodic condition of aluminate solutions to a silicate gel mixture. In spite of the poor match of addition rate with crystallization rate, as in Examples 4 and 7, the $SiO_2/Al_2O_3$ ratio of the final product was substantially the same as the better matched preparations. Furthermore, with no increase in the crystallinity of the solid phase, X-ray examination of the intermediate samples of Example 4 showed that the $SiO_2/Al_2O_3$ ratio of the crystalline phase continually changed with the availability of aluminum species. This experimental evidence appears to suggest that there is a dynamic equilibrium between the crystalline phase and the amorphous phase during the crystallization process.

The present study shows that a zeolite ZSM-5 having a high $SiO_2/Al_2O_3$ mole ratio of, for example, 70 can be synthesized at 1 atmosphere by adding a small fraction of the aluminate solution at the beginning of the synthesis and the nucleation time can be shortened to 3–4 days, i.e. only 1/10th of the time required if all the aluminate were added at once.

Steam stability tests were conducted on a HZSM-5 sample made from the product of Example 5, which was crystallized under well matched conditions. The data, as shown in Table III, showed a small improvement in steam stability when compared to the commercial catalyst of HZSM-5 prepared by conventional technique. Catalytic activity was evaluated employing n-hexane cracking in the "alpha" test, described by P. B. Weisz and J. N. Miale in "Journal of Catalysts", Volume 4, Number 4, August 1965, pp. 527–9.

TABLE III

| Steaming Test at 1 atm., 100% Steam | | |
|---|---|---|
| | Alpha Value | |
| | 4 hours at 950° F | 15 hours at 1000° F |
| HZSM-5 from Example 5 | 36 | 13 |
| Commercial Catalyst | 35 | 12 |

Alpha at 1000° F, corrected to 0.42 g. zeolite.

What is claimed is:

1. A method for preparing crystalline aluminosilicate zeolites having a silica/alumina mole ratio of greater than 10 from an amorphous mixture of reaction components which comprises forming an amorphous mixture containing sources of an alkali metal oxide, an organic nitrogen-containing oxide, an oxide of silicon and water and having a composition in terms of mole ratios of oxides, as follows:

| $OH^-/SiO_2$ | = | 0.01 – 0.5 |
|---|---|---|
| $Al_2O_3/SiO_2$ | = | 0 – 0.01 |
| $H_2O/OH^-$ | = | 50 – 500 |
| $M_2O/SiO_2$ | = | 0.01 – 1.0 |
| $R_2O/SiO_2$ | = | 0.01 – 0.5 | wherein R is an organic nitrogen-containing cation and M is an alkali metal ion, and while maintaining the mixture at a temperature of from about 180° F to about 400° F until crystals of the aluminosilicate zeolite are formed, adding to said mixture a source of aluminum ions at a rate of addition whereby the concentration of aluminum ions in the amorphous mixture is maintained at steady state during crystallization of aluminosilicate zeolite therefrom, thereby maintaining any excess of aluminum ions in said mixture at a minimum by replenishing same at about the same rate as the rate of their consumption during crystallization.

2. The method of claim 1 wherein the zeolite prepared is ZSM-5 and wherein R is a tetrapropylammonium ion and M is an alkali metal ion.

3. The method of claim 1 wherein the zeolite prepared is ZSM-11 and wherein R is a tetrabutylammonium ion or a tetrabutylphosphonium ion and M is an alkali metal ion.

4. The method of claim 1 wherein the zeolite prepared is ZSM-12 and wherein R is a tetraethylammonium ion and M is an alkali metal ion.

5. The method of claim 1 wherein the zeolite prepared is ZSM-23 and wherein R is a cation derived from pyrrolidine and M is an alkali metal ion.

6. The method of claim 1 wherein M is sodium.

7. The method of claim 2 wherein M is sodium.

8. The method of claim 3 wherein M is sodium.

9. The method of claim 4 wherein M is sodium.

10. The method of claim 5 wherein M is sodium.

11. The method of claim 1 wherein said source of aluminum ions is sodium aluminate, aluminum oxide or aluminum sulfate.

12. The method of claim 2 wherein said source of aluminum ions is sodium aluminate, aluminum oxide or aluminum sulfate.

13. The method of claim 3 wherein said source of aluminum ions is sodium aluminate, aluminum oxide or aluminum sulfate.

14. The method of claim 4 wherein said source of aluminum ions is sodium aluminate, aluminum oxide or aluminum sulfate.

15. The method of claim 5 wherein said source of aluminum ions is sodium aluminate, aluminum oxide or aluminum sulfate.

* * * * *